(12) United States Patent
Fischer et al.

(10) Patent No.: US 7,338,669 B2
(45) Date of Patent: Mar. 4, 2008

(54) INORGANIC BORANOPHOSPHATE SALTS

(75) Inventors: Bilha Fischer, Shoham (IL); Victoria Nahum, Rishon Lezion (IL)

(73) Assignee: Bar-Ilan University, Ramat-Gan (IL)

( * ) Notice: Subject to any disclaimer, the term of this patent is extended or adjusted under 35 U.S.C. 154(b) by 3 days.

(21) Appl. No.: 10/588,074

(22) PCT Filed: Feb. 2, 2005

(86) PCT No.: PCT/IL2005/000118

§ 371 (c)(1),
(2), (4) Date: Jul. 31, 2006

(87) PCT Pub. No.: WO2005/072062

PCT Pub. Date: Aug. 11, 2005

(65) Prior Publication Data

US 2007/0160682 A1    Jul. 12, 2007

(51) Int. Cl.
*A61K 33/42* (2006.01)
*C01B 35/10* (2006.01)

(52) U.S. Cl. ............... 424/601; 423/277; 536/26.1

(58) Field of Classification Search ........... 424/601; 423/277; 536/26.1
See application file for complete search history.

(56) References Cited

U.S. PATENT DOCUMENTS

| | | | | |
|---|---|---|---|---|
| 5,264,602 A | * | 11/1993 | Juge et al. | 556/402 |
| 5,434,285 A | * | 7/1995 | Laffitte et al. | 556/402 |
| 6,140,537 A | * | 10/2000 | Katoh et al. | 564/8 |
| 2004/0097719 A1 | | 5/2004 | Agrawal et al. | |

FOREIGN PATENT DOCUMENTS

WO    WO-2004/044136 A2    5/2004

OTHER PUBLICATIONS

Tsuneo Imamoto et al., "Boranophosphorylation Reagents, Dimethyl Boranophosphate Monopotassium Salt and Tetramethyl Boranopyrophosphate", *J. Am. Chem. Soc.*, 1997, vol. 119, pp. 9925-9926.

Hong Li et al., "Hydrolysis of Thymidine Boranomonophosphate and Stepwise Deuterium Substitution of the Borane Hydrogens. $^{31}$P and $^{11}$B NMR Studies", *J. Am. Chem. Soc.*, 1996, vol. 118, pp. 6606-6614.

Vladimir Rait et al., "Boranophosphate Nucleic Acids—A versatile DNA Backbone", *Nucleosides & Nucleotides*, 1999, vol. 18. pp. 1379-1380.

Barbara Ramsey Shaw et al., "[13] Boranophosphate Backbone: a Mimic of Phosphodiesters, Phosphorothioates, and Methyl Phosphonates", *Methods in Enzymol*, 2000, vol. 313, pp. 226-257.

Anup Sood et al., "Boron-Containing Nucleic Acids. 2.[1] Synthesis of Oligodeoxynucleoside Boranophosphates", *J. Am. Chem. Soc.*, 1990, vol. 112, pp. 9000-9001.

Jack S. Summers et al., "Structural Stidues of a Borane-Modified Phosphate Diester Linkage: An Initio Calculations on the Dimethylboranophosphate Anion and the Single-Crystal X-ray Structure of Its Diisopropylammonium Salt", *Inorg. Chem.*, 1998, vol. 37, pp. 4158-4159.

Gregory R. J. Thatcher et al., "Phosphonates as Mimics of Phosphate Biomolecules: Ab Initio Calculations on Tetrahedral Ground States and Pentacoordinate Intermediates for Phosphoryl Transfer", *J. Org. Chem.*, 1993, vol. 58, pp. 2272-2281.

Takeshi Wada et al., "A new boranophosphorylation reaction for the synthesis of deoxyribonucleoside boranophosphates", *Tet. Lett.*, 2002, vol. 43, pp. 4137-4140.

Jiancun Zhang et al., "Synthesis and Hybridization Study of a Boranophosphate-Linked Oligothymidine Deoxynucleotide", *Tet. Lett.*, 1997, vol. 38, No. 28, pp. 4957-4960.

* cited by examiner

*Primary Examiner*—Yvonne (Bonnie) Eyler
*Assistant Examiner*—Chukwuma O. Nwaonicha
(74) *Attorney, Agent, or Firm*—Browdy and Neimark, PLLC

(57) ABSTRACT

The invention provides novel inorganic boranophosphate salts that can be used as fertilizers, in detergent formulations, as additive in melts for the glass industry, in boron neutron-capture therapy of cancer, and as synthetic building blocks in the synthesis of boranonucleotides of various lengths.

8 Claims, 5 Drawing Sheets

INORGANIC BORANOPHOSPHATE SALTS

FIELD OF THE INVENTION

The present invention relates to inorganic boranophosphate salts, that are phosphate mimic, and to their preparation and uses.

BACKGROUND OF THE INVENTION

The quest for phosphate bioisosters over the last several decades included the synthesis of phosphonates, α-halo (e.g. difluoromethyl) phosphonates (Blackburn, 1981; Blackburn et al., 1981 and 1987), phosphorothioates (Nahorski and Potter, 1989; Eckstein, 1983, 1985, and 2000) and boranophosphate analogues (Sood et al., 1990; Summers et al., 1998; Shaw et al., 1993 and 2000).

Phosphates and phosphate-containing molecules play a major role in numerous biological systems (Westheimer, 1987 and 1992). However, the unwanted lability of the ester P—O bond has promoted the search for suitable bioisosters, phosphate analogues, which retain biological activity but possess diminished lability. The search for bioisosters was initiated by the need to produce phosphate probes for various studies, such as probing stereochemical requirements of enzymes (Roumaniuk and Eckstein, 1981; Conolly and Eckstein, 1982). In addition, phosphate bioisosters have been developed for improving the pharmacological effects of nucleotide-based drugs, e.g. anti-sense agents (Agrawal, 1999; Stein, 1996).

A widely used isoster of phosphate is phosphorothioate and its analogues, proposed in the pioneering work of Eclkstein et al. (Nahorski and Potter,1989; Eckstein, 1983, 1985, and 2000). In these analogues, the nonbridging oxygen atom is replaced by a sulfur atom. Other chemical modifications of the phosphate moiety include the substitution of the labile phosphate ester oxygen atom by carbon or nitrogen atom, to give phosphonates and phosphoramidate analogues, respectively (Engel, 1977).

During the last decade, pioneering studies by Spielvogel and Ramsay-Shaw have proposed boranophosphate analogues 1 as bioisosters of natural nucleotides (Sood et al., 1990; Shaw et al., 2000) and as important tools for biochemists (Rait et al., 1999; Zhang et al., 1997; Porter et al., 1997).

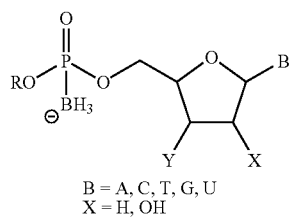

B = A, C, T, G, U
X = H, OH
1a. Y = OH; R = H
1b. Y = OH; R = $P_2O_6^{3-}$
1c. Y = OH; R = $PO_3^{2-}$
1d. Y = OH; R = 3'-nucleoside
1e. Y = OH; R = 3'-oligonucleotide
1f. R = 3'-ribose This new class of boron modified nucleotides, that mimic phosphodiesters, phosphorothioates, and methyl phosphonates, was designed for use as potential therapeutic and diagnostic agents. These nucleoside boranophosphates, or borane phosphonates, have a borane moiety ($BH_3$) in replacement of one of the nonbridging oxygen atoms in the phosphate diester moiety. The $BH_3$ group maintains the negative charge of a phosphate, but it does not form classical H-bonds and does not coordinate with metal ions. This modification imparts unique characteristics to boranophosphate nucleotides and nucleic acids. The boranophosphate can be considered as a "hybrid" of three well-studied types of modified phosphates, namely, normal phosphate, phosphorothioate, and non-ionic methylphosphonate. The $BH_3$ group in the boranophosphates is isoelectronic with oxygen (O) in the normal phosphates, and isolobal (pseudo-isoelectronic) with sulfur (S) in phosphorothioates. The $BH_3$ group is isosteric with the $CH_3$ group in the methylphosphonates. Boranophosphates would be expected to share a number of chemical and biochemical properties with phosphorothioate and methylphosphonate analogs. Thus, boranophosphate analogues have a different charge distribution and polarity than the corresponding natural nucleotides (Shaw et al., 1993).

This emerging field of novel nucleotide bioisosters has expanded significantly and has provided many important applications of the boranophosphate analogues. For instance, non-terminal P-boronated nucleotides, existing as a pair of diastereoisomers, have been used as stereochemical probes to elucidate enzymatic catalysis (Sergueeva et al., 2000). Oligodeoxyribonucleotides bearing boranophosphate linkages have been used for polyrnerase chain reaction (PCR) sequencing and DNA diagnostics (He et al., 1999; Porter et al., 1997), and boranophosphate nucleotides have been found to be highly potent and stable P2Y-receptor agonists (Nahum et al., 2002). Oligonucleotides bearing boranophosphate linkages have also been considered as potentially useful anti-sense agents (Summers and Shaw, 2001). These analogues were also tested for the treatment of cancer as carriers of $^{10}$B isotope in boron neutron capture therapy (Spielvogel et al., 1992). However, despite the extensive study of related boranophosphate nucleotide/oligonucleotide analogues, the exploration of the parent inorganic boranophosphate has not been reported.

The various potential applications of a phosphate isoster, together with the limitations of the currently available isosters, justify the continued search for the perfect inorganic phosphate mimic.

SUMMARY OF THE INVENTION

It has now been found, in accordance with the present invention, that the inorganic boranophosphate 2, herein designated BPi, is a phosphate mimic.

The present invention thus relates to salts of the inorganic boranophosphate of the general formula 2, herein designated BPi salts, wherein M is a counterion.

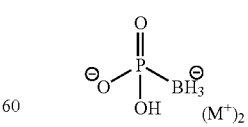

2

In one embodiment, the counterion M is ammonium ($NH_4^+$) or it is an inorganic cation derived from an alkali, alkaline earth or transition metal such as, but not limited to, $Na^+$, $K^+$, $Li^+$, $Ca^{++}$, $Mg^{++}$, $Ni^{++}$, $Cu^{++}$, $Fe^{++}$, $Fe^{+++}$, $Co^{++}$, $Zn^{++}$, $Pd^{++}$, and $Ag^+$.

In another embodiment, the counterion M is an organic cation derived from an amnine of the formula $R_3NH^+$, wherein R is $C_1$-$C_{18}$, preferably $C_1$-$C_6$, alkyl, more preferably ethyl, propyl or butyl, or two of the Rs together with the nitrogen atom to which they are attached form a 3-7 membered ring optionally containing a further heteroatom selected from the group consisting of N, S and O, such as for example pyrrolydine, piperidine, morpholine, or R is phenyl or heteroaryl such as pyridyl, imidazolyl, pyrimidinyl, and the like.

The present invention further relates to a method for the preparation of BPi salt in a one-pot two-step reaction comprising reacting tris(trimethylsilyl)-phosphite with borane-dimethylsulfide complex of the formula $BH_3.SMe_2$, reacting the intermediate 11 (see Scheme 2 hereinafter) with the desired base in water or in methanol, thus obtaining the corresponding salt of BPi in very high yield.

In one embodiment, the intermediate 11 is treated with methanolic ammonia or with an aqueous $NH_4OH$ solution, thus resulting in the ammonium salt of BPi, 2a. In another embodiment, the intermediate 11 is treated with tributylamine, $Bu_3N$, in methanol, thus resulting in the $Bu_3NH^+$ salt of BPi, 2b. In a further embodiment, the intermediate 11 is treated with triethylammonium bicarbonate buffer, thus resulting in the $Et_3NH^+$ salt of BPi, 2c.

In another embodiment, the compound 2a is passed through a Sephadex-CM C-25-tetraethylammonium-form column, thus resulting in the $Et_4N^+$ salt of BPi, 2d.

The present invention further relates to the use of the boranophosphate salts of the invention as fertilizers, in detergent formulations, as additive in melts for the glass industry, in boron neutron-capture therapy (BNCT) of cancer, and as synthetic building blocks in the synthesis of boranonucleotides that may be used for all the uses known today and that may be discovered in the future for boranonucleotides of various lengths.

BRIEF DESCRIPTION OF THE FIGURES

FIG. 1A: $^1H$ decoupled $^{31}P$ NMR spectrum in $D_2O$ at 81 MHz; FIG. 1B: $^1H$ coupled $^{31}P$ NMR spectrum in $D_2O$ at 81 MHz; FIG. 1C: $^1H$ NMR spectrum in $D_2O$ at 200 MHz.

FIG. 3A: Unit cell includes 8 BPi molecules, 8 H-phosphonate molecules, and 24 ammonium ions; hydrogen -atoms are omitted to clarify the Bpi geometry; FIG. 3B ORTEP drawing of BPi; crystal data of 2a: monoclinic, $P2_1/c$; a=23.616(5) Å, b=6.3470(13) Å, c=15.325(3) Å; V=2172.9(8) Å$^3$; Z=12; $D_{calcd}$=1.623 g/cm3; F(000)=1104; 3094 reflections collected, R=0.1015, Rw=0.2345, GOF=1.286; Selected bond lengths [Å] and angles [°]: P(1)-O(1A) 1.524(7), P(1)-O(1B) 1.617(7), P(1)-O(1C) 1.583(7), P(1)-B(1) 1.891(11); O(1A)-P(1)-O(1C) 104.0(4), O(1A)-P(1)-O(1B) 105.3(4), O(1C)-P(1)-O(1B) 104.4(4), O(1A)-P(1)-B(1) 118.2(5), O(1C)-P(1)-B(1) 113.0(5), O(1B)-P(1)-B(1) 110.7(5)

DETAILED DESCRIPTION OF THE INVENTION

Figure 1A:
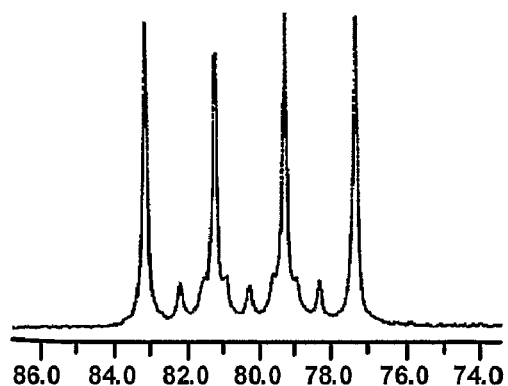
FIGS. 1A-1C show the NMR spectra of BPi.

The present invention relates to the preparation, characterization, and unique chemical properties of inorganic boranophosphate (BPi) salts. As shown herein, the BPi ion is an excellent mimic of inorganic phosphate.

The unique and chemically interesting inorganic boranophosphate BPi was investigated here as a mimic of phosphate with respect to properties such as water solubility, geometry, acid/base character, H-bonding and chemical reactivity. The great similarity of BPI to the inorganic phosphate, Pi, is demonstrated here by the BPi's high water solubility, and geometry that is in accordance with that of the parent, except for the long P—B bond (1.892 Å) and B—P—O angles that are slightly larger than tetrahedral angles. Furthermore, the acid/base character of BPi is essentially not altered in comparison to Pi. This finding is in contrast to the corresponding phosphorothioate isoster, where there is a reduction of about two log units in the acidity relative to Pi (Jaffe and Cohn, 1978; Gerlt et al., 1983). Likewise, $pK_{a2}$ values of α-mono- and di-fluorophosphonate isosters are one and two log units, respectively, lower than $pK_{a2}$ of phosphoric acid (Blackburn et al., 1987).

BPi is stable under both highly basic and acidic conditions (at pH>2). In addition, BPi is stable in the presence of imidazole, pyridine and divalent metal ions such as $Zn^{2+}$ and $Mg^{2+}$ ions. However, the P—B bond cleavage is observed upon the reaction of BPi with carbodiimides or upon catalytic hydrogenation. A loss of BOP's borane moiet also occurs at pH values below 2.

A drastic alteration in the chemical nature of BPi as compared to Pi and $BH_3$ complexes is observed. While Pi is a nucleophile (Saxena, 2002; El Seoud et al., 2002; Cullis et al., 2001; Bundgaard and Hansen, 1981), BPi is a poor nucleophile. Likewise, the reducing nature of the $BH_3$ group in BPi is drastically lower than in other $BH_3$ complexes.

The compounds 2 of the invention are all inorganic boranophosphate salts having different ammonium counterions (ammonium in 2a, tributylammonium in 2b, triethylammonium in 2c, and tetraethylammonium in 2d).

Based on the geometry, water solubility, acid-base character, and H-bonding properties, BPi appears to be perfect mimic of Pi, and is an attractive alternative to the known phosphate (thiophosphate and α-halophosphonate) isosters, and therefore, may have numerous promising applications ranging from biochemical probing to modulation of materials properties.

As mentioned above, the field of boranophosphates deals extensively with the related nucleotide/oligonucleotide analogues. However, to the best of our knowledge, no attention has been given to the unique and chemically interesting inorganic boranophosphate 2, BPi.

The existence of BPi in the free form, $BH_3O_3P$ (CAS No. 178449-22-4), has been detected previously (Li et al., 1996), while carrying out the hydrolysis of thymidine boranomonophosphate in neutral solution. The compound was not stable: its NMR was determined in the solution, and it decomposed before it could be isolated.

Although the related dimethyl boranophosphate potassium salt 3, has been described by Imamoto et al. (1997) and by Wada and Saigo (Wada et al., 2002), the preparation of stable salts of inorganic boranophosphate 2, has not been reported to our knowledge.

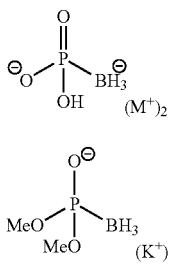

Numerous applications can be envisaged for the boranephosphates BPi, and all of them are encompassed by the present invention.

Among the essential elements required for plants growth are: P (macronutrient, 0.2 wt %) and B (micronutrient, 20 ppm). Likewise, K and N are also essential nutrients (1.0 and 1.5 wt %, respectively). Therefore, ammonium or $K^+$ salt of BPi may be used in formulations of fertilizers. These salts provide the essential nutrients P, B, and N or K; they are non-acidic, water-soluble, and have a high phosphorous content.

The BPi salts of the invention can also be used for specialized detergent formulations. For this application, BPi should be provided in the form of the corresponding pyrophosphate or tri-phosphate. Such oligoboranophosphates are expected to soften hard water by sequestering undesired $Ca^{2+}/Mg^{2+}$ ions. The high charge on the phosphate chain helps to stabilize detergent micelles (as a 'builder'). Oligoboranophosphates provide the correct pH for cleaning (slightly basic). Furthermore, in warm/hot water ($\geq 50°$ C.), boric acid is produced from hydrolysis of BPi and exerts its effect as a bleaching agent.

The BPi salts of the invention may also serve as an interesting additive in melts for glass making. For comparison, high quality borophosphate chemically durable optical glass is obtained from: $MgO/Al_2O_3/K_2O/B_2O_3/P_2O_5$ melts.

The natural boron isotope $^{10}B$ absorbs thermal neutrons. Upon capturing a thermal neutron, $^{10}B$ undergoes fission to generate $^{7}Li$ nucleus and energetic alpha (helium) particles, which are highly destructive within their relatively short path (10-14 mm). The specific localization of boron in rapidly dividing cells such as tumor cells is useful for destroying these cells by using Boron Neutron-Capture Therapy (BNCT), without affecting normal cells. BNCT requires about 5 ppm $^{10}B$. Therefore, the BPi salts of the invention, which are transported to the rapidly dividing cells, can be useful as BNCT agents for treatment of tumors. The invention thus comprises the use of a boranophosphate salt as described herein for the manufacture of a pharmaceutical preparation for boron neutron capture therapy (BNCT) of cancer.

Since the BPi salts of the invention are mimics of natural phosphodiesters in DNA, they can be used as synthetic building blocks for biologically active borano nucleosides and nucleotides of various lengths (mono-, di- and oligo-nucleotides) and designed for use as potential therapeutic and diagnostic agents, and this aspect is also encompassed by the invention. Regarding therapeutic use, we have disclosed (Nahum, 2002, WO 03/034978) that ATP-α-Boron analogues are potent $P2Y_1$-R (ATP receptor) agonists and can be utilized as therapeutic agents for the treatment of Type II diabetes.

The boranonucleotides obtained from the inorganic boranophosphate salts of the invention can be used in all known and future applications of borano nucleotides. For example, non-terminal P-boronated nucleotides can be used as stereochemical probes to elucidate enzymatic catalysis. The oligodeoxyborano-ribonucleotides can be used for polymerase chain reaction (PCR) sequencing and DNA diagnostics. The oligoboranonucleotides can be useful as anti-sense agents targeting specific MRNA sequences, as inhibitors of ATP-utilizing enzymes (e.g. NTPDase) that are involved in various health disorders, and also in the treatment of cancer as carriers of $^{10}B$ isotope in boron neutron capture therapy.

The borano nucleotides may be prepared by any suitable synthetic method, for example as described in Sood et al. (1990), Summers and Shaw (2001) and WO 95/06752 (Shaw and Porter).

The invention will now be illustrated by the following non limiting Examples.

EXAMPLES

Experimental
(i) General.

All air- and moisture-sensitive reactions were performed in flame-dried, nitrogen flushed flasks sealed with rubber, septa; the reagents were introduced with a syringe. The progress of the reactions was monitored by TLC on pre-coated Merck silica-gel plates (60 K-254). Column chromatography was performed with Merck silica gel 60 (230-400 mesh). Compounds were characterized by nuclear magnetic resonance (NMR) spectroscopy using Bruker DPX-300, DMX-600, or AC-200 spectrometers. NMR spectra were recorded with a Bruker AC-200 spectrometer with a $^{31}P$ NMR probe (isotope frequency of 81 MHz) using 85% $H_3PO_4$ as an external reference. IR spectra of BPi in KBr pellets were recorded with a Nicolet Impact 400D spectrometer using the OMNIC program. IR spectra of BPi in solution were measured using a Bruker Vector 22 equipped with a liquid nitrogen cooled MCT detector. For the ATR measurements, a Harrick variable angle ATR accessory was used. For one spectrum, 100 scans were coadded at a resolution of 4 $cm^{31\ 1}$. The clean ATR Germanium crystal (Harrick Scientific Corporation) was measured for the background spectra (cutoff 680 $cm^{-1}$). Crystallographic data were collected with a Nonius KappaCCD diffractometer at 120K with scans of 1° collected at a speed of 1°/20 sec; the merging R-factor on the data was 0.046 with 36867 reflections collected and 2979 unique. Bpi crystals were obtained as colorless needles. Further details of the crystal structure investigation may be obtained from the Fachinformationzentrum Karlsruhe, 76344 Eggenstein-Leopoldshafen, Germany, on quoting the depository number CSD-413735. Melting points were measured using a Fisher-Johns melting point apparatus. Apparent pH values were measured with a Hanna Instruments pH-meter (HI 8521), equipped with an Orion micro-combination pH electrode (9802).

(ii) Synthesis of Dibenzyl Boranophosphate 9__

The synthesis was carried out according to Scheme 1B hereinafter. To a solution of dibenzylphosphite (300 μL, 1.186 mmol) in dry THF N, O-bis(trimethylsilyl)acetamide (880 μL, 3.56 mmol) was added with pippetor and the mixture was stirred for 25 min at room temperature. The solution was cooled to 0° C., and 2M $BH_3.SMe_2$ complex in THF (2.9 mL, 5.8 mmol) was added. The solution was stirred at room temperature for 15 min, and then evaporated. 24% $NH_4OH$ solution (6 mL) was added and the mixture was stirred at room temperature for 1 h, and then freeze-dried. The product was purified by silica gel column chromatography (elution with $CHCl_3$: MeOH, 12:1) and obtained as colorless oil in 71% yield (231 mg, 0.84 mmol). $^1H$ NMR ($CDCl_3$, 300 MHz): δ 7.22 (s), 4.86 (m), 0.3 (1-1-1-1 quartet) ppm. $^{31}P$ NMR ($CDCl_3$, 81 MHz): δ 97.5 (q) ppm. MS FAB (negative) m/z: 275.140 ($M^-$).

Example 1

Synthesis of BPi Salts

For the preparation of boranophosphate BPi, we first attempted the treatment of chlorobis(di-isopropylamino)phosphane 4 with borane dimethylsulfide ($BH_3 \cdot SMe_2$) complex (Longeau and Knochel, 1996), followed by acidic hydrolysis (pH 3 or 1) for several hours, according to Scheme 1A below. This attempt resulted in a mixture of several phosphorus species but BPi was not obtained.

In an alternative approach, depicted in Scheme 1B below, dibenzyl H-phosphonate 6 was treated with bis(silyl)acetamide (BSA) in THF, followed by boranation of the intermediate 7 with $BH_3 \cdot SMe_2$ complex, and hydrolysis of compound 8 with concentrated ammonium hydroxide for 1 h. In this way, dibenzyl boranophosphate 9 was obtained in 71% overall yield (Scheme 1B). However, attempts to remove the benzyl groups by either catalytic hydrogenation or acidic hydrolysis (pH=1.3), resulted in the cleavage of the P—B bond, leading to phosphorus acid instead of BPi.

Scheme 1

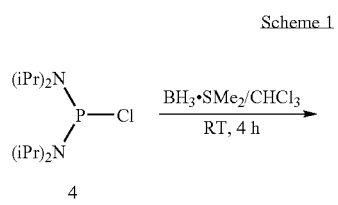

A

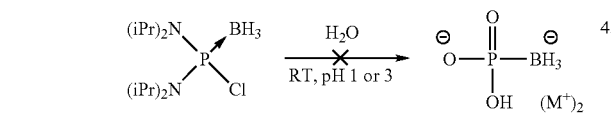

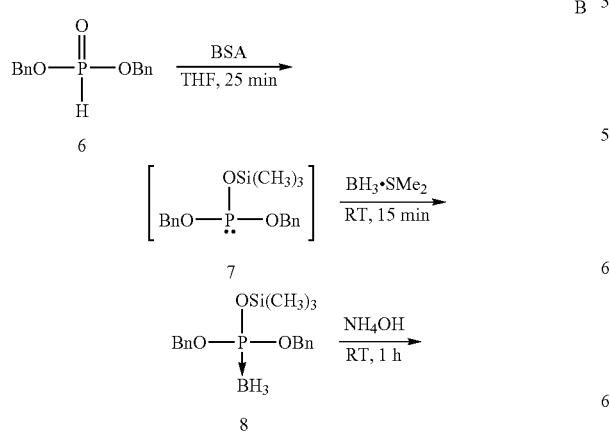

B

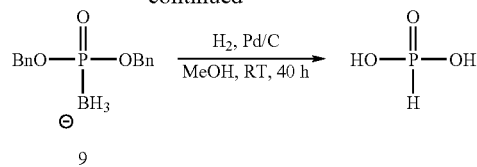

9

Eventually, we were able to obtain BPi in an excellent overall yield in a two-step, one-pot reaction starting from tris(trimethylsilyl) phosphite (Sood et al., 1991) 10 (Scheme 2). Phosphite 10 was treated with $BH_3 \cdot SMe_2$ complex in dry acetonitrile under an inert gas for 15 minutes. Subsequently, intermediate 11 was treated with 2 M methanolic ammonia for 1 h to give the ammonium salt BPi 2a, as a white solid in 93% yield. No further purification was conducted, since volatile silyl derivatives 10 and the unreacted $BH_3 \cdot SMe_2$ were removed by evaporation. Alternatively, intermediate 11 was treated with $NH_4OH_{(aq)}$ solution (pH=10), tributylamine ($Bu_3N$) in MeOH, or 0.5 M triethylammonium hydrogencarbonate buffer (pH=7.5) and freeze-dried or concentrated to provide the corresponding BPi salts 2a, 2b or 2c, respectively.

Scheme 2

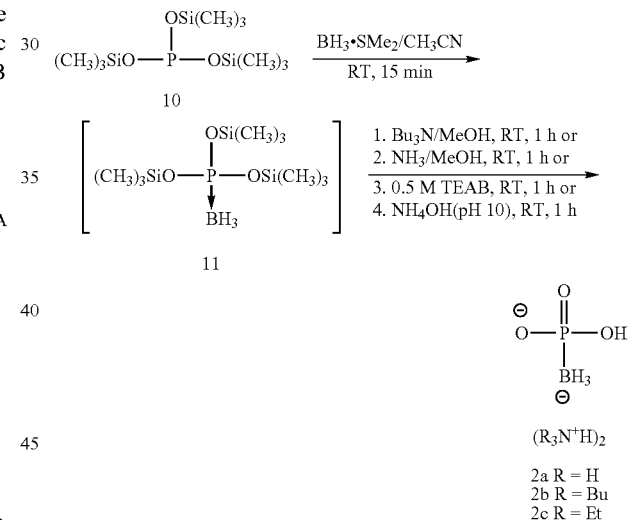

Product 2a is highly water-soluble, whereas 2b dissolves only in organic solvents such as MeOH, $CH_3CN$, DMF, and $CHCl_3$. Product 2c is highly soluble both in water and in organic solvents.

Example 2

Synthesis and Characterization of Compounds 2a, 2b and 2d

2(i) Synthesis of Ammonium Boranophosphate 2a.

The synthesis was carried out according to Scheme 2 hereinabove. To a solution of tris(trimethylsilyl)phosphite (600 μL, 1.795 mmol) in dry $CH_3CN$ (5 mL) under $N_2$ at 0° C., $BH_3 \cdot SMe_2$ complex in THF (2M, 1.35 mL, 2.7 mmol) was added. The resulting solution was kept at room temperature for 15 min. Dry MeOH (15 mL) and 2 M NH3 in EtOH (1.8 mL, 3.6 mmol) were added and the mixture was stirred at room temperature for 1 h. The solvent was removed under reduced pressure and the product was obtained as a white solid in 93% yield (202 mg, 1.556 mmol), mp>240° C. $^1$H NMR (D$_2$O, 200 Hz): δ 0.27 (d of 1-1-1-1 quadruplet, $J_{P,H}$=22, $J_{B,H}$ =87 Hz, 3 H). $^{31}$P NMR (D$_2$O, 81 MHz): δ 80.38 (1-1-1-1 quadruplet, J=156 Hz, 1-1-1-1-1-1-1 septuplet, J=52 Hz) ppm. IR (KBr): ν 2412, 2378, 2352, 1181, 1149, 1077-903, 654 cm$^{-1}$.

2(ii) Synthesis of Tetraethylammonium Boranophosphate 2d.

Compound 2a was converted to the corresponding tetraethylammonium salt as follows: 2a was passed through a Sephadex-CM C-25—tetraethylammonium-form column (prepared from the corresponding sodium form resin upon loading with excess Et$_4$NCl) and the column was washed with about 20 volumes of deionized water. The solution was freeze-dried to yield tetraethylammonium BPi, 2d, as a white solid. Based on the pH value of the 2d solution, the $^{31}$P NMR spectrum, and correlation with the plot of BPi $^{31}$P NMR shifts vs. pH (FIG. 5), the expected empirical formula is BH$_3$O$_3$PH$_{1.5}$(Et$_4$N)$_{1.5}$(289.3): calcd. H 11.9, P 10.7; found H 11.3; P9.5.

2(iii) Synthesis of Tributylammonium Boranophosphate 2b.

The tributyl ammonium salt of the inorganic boranophosphate was prepared as described above for 2a. However, Bu$_3$N (0.85 mL, 3.57 mmol) was added instead of NH$_3$/EtOH. The product was obtained as a white solid in 93% yield (645 mg, 1.385 mmol), m.p. 83-84° C. IR(KBr): ν: 2407, 2381, 2350, 1184, 1150, 1100-850, 655 cm$^{-1}$.

2(iv) Determination of the pK$_a$ Values of Boranophosphate 2a.

The pK$_a$ values of 2a were evaluated by $^{31}$P NMR spectroscopy at room temperature. Solutions of 2a (0.15-0.18 M) at different pH values were prepared by adding dilute sodium hydroxide or hydrochloric acid solutions. The $^{31}$P NMR chemical shift was monitored as a function of the pH. A five-parameter sigmoid function was fitted to the data using Sigma Plot 2000 (SPSS, Inc.):

$$\delta = \delta_0 + a/[1+e^{-((pH-pH0)/b)}]^c$$

The inflection point, which is determined by the second derivative of the fitted sigmoid function, is the pK$_a$ value.

2(v) Determination of the Decomposition Rate of BPi 2a at pH=2.

The stability of 2a in acidic solution was evaluated by $^{31}$P NMR spectroscopy at room temperature, monitoring the formation of the deboranation product (phosphorus acid). A 0.16 M solution of 2a at pH 2 was prepared by adding dilute hydrochloric acid to a solution of inorganic boranophosphate (NH$_4^+$salt) in H$_2$O and 10% D$_2$O. The percentage of decomposition of 2a is based on integrations of PBi and phosphorus-acid signals (δ=90.93 and 3.3 ppm, respectively). The decomposition rate was determined by measuring changes in the integration of the respective NMR signals within 96 h.

2(vi) NMR Spectroscopy of Compound 2a.

Figure 1B:
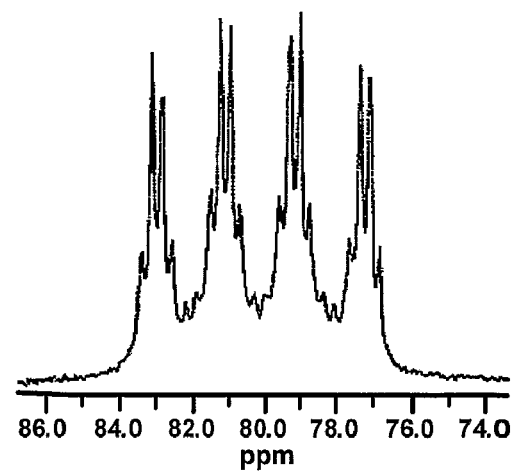
Figure 1C:
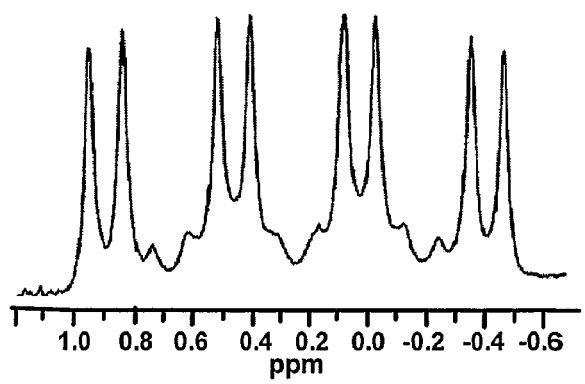

Compound 2a in water was characterized by $^{31}$P NMR spectroscopy showing a signal at δ≈80 ppm (FIG. 1). The boranophosphate $^{31}$P NMR spectrum shows a typical pattern including two overlapping signals: the larger signal is due to coupling of P to the $^{11}$B isotope, and the smaller signal is due to coupling with $^{10}$B isotope. The relative height of the smaller peak to the larger one is 0.14 (FIG. 1A) (Harris, 1986). BPi's hydrogen-coupled $^{31}$P NMR spectrum shows further splitting of the lines into a quadruplet (FIG. 1B). The $^1$H NMR spectrum shows a typical doublet of quadruplets pattern, at δ≈0.2 ppm, due to coupling of H to both $^{11}$B and $^{31}$P (FIG. 1C). This pattern overlaps a more complex pattern due to coupling of H to both $^{10}$B and $^{31}$P.

Figure 2:
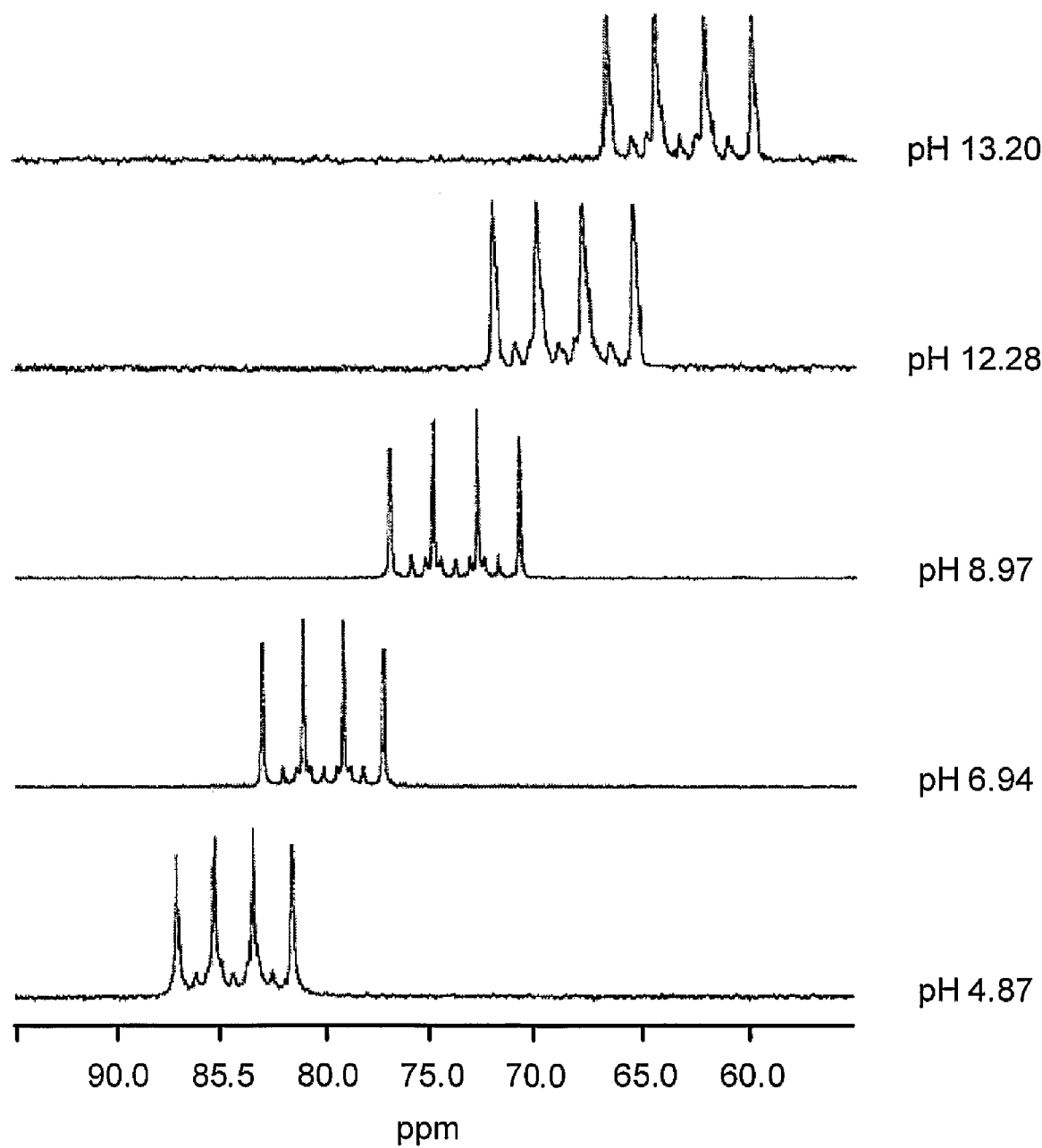
FIG. 2 shows the pH-dependent $^{31}P$ NMR chemical shift of BPi in $H_2O$ within the pH range 4.87-13.20 at 81 MHz.

The chemical shift of BPi is pH-dependent. For instance, at pH 4.87 and 13.20 the phosphorus atom of BPi resonates at δ=84 and 63 ppm, respectively (FIG. 2). Likewise, the P—B coupling constant is also pH-dependent, and is reduced as the pH decreases (e.g. 147 and 183 Hz for pH 4.87 and 13.2, respectively). The pH-dependent BPi spectrum indicates structural changes of BPi, which are due to the reduction of O—P—O angles upon protonation of the molecule.

2(iii) X-ray Crystallography of 2a.

To obtain structural information on BPi, compound 2a was crystallized from an aqueous solution (pH=7). In addition to compound 2a, the crystal contained phosphorus acid (H-phosphonate) in a 1:1 ratio. This unexpected ratio does not reflect the molar ratio in the original BPi solution, in which phosphorus acid was less than 5%.

Figure 3A:
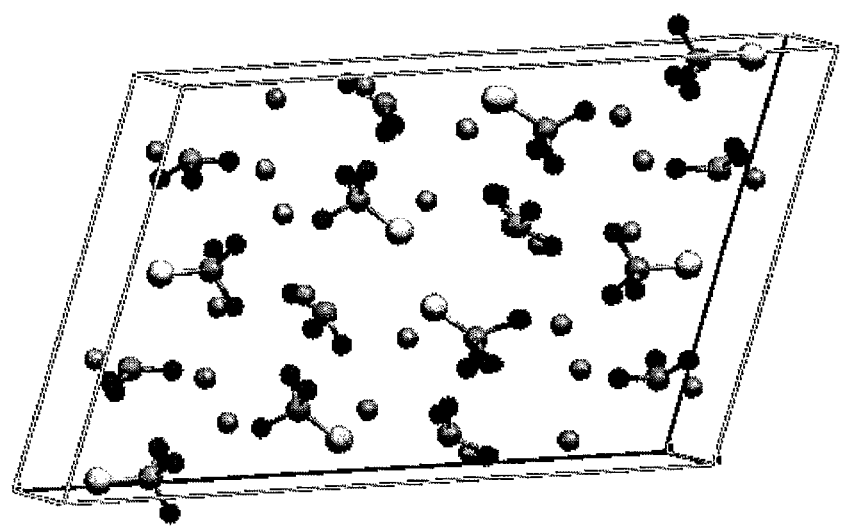
FIGS. 3A-3B show the X-ray structure of BPi.

The unit cell contains 8 BPi ions, 8 H-phosphonate ions, and 24 ammonium ions (FIG. 3A). Apparently, for each BPi anion, one ammonium counterion is observed, whereas two ammonium counterions are observed around each H-phosphonate group.

Figure 3B:
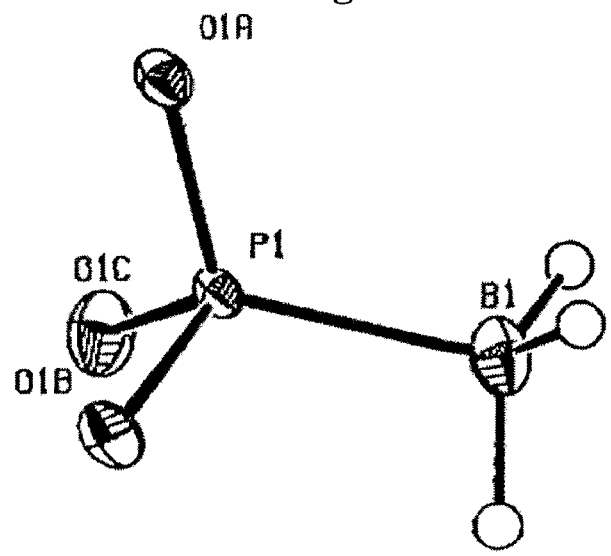

For BPi, the average P—B bond length is 1.892 Å, whereas for the three P—O bonds, the average lengths are: 1.585, 1.605 and 1.524 Å, respectively (FIG. 3B). A deviation from tetrahedral angles was observed with values of 111-118° for B—P—O and 104-105° for O—P—O angles.

Comparison with X-ray crystal data obtained for the related dimethyl boranophosphate salt, 3 (Imamoto et al., 1997), indicated similar values for the B—P (1.895 Å) and O—P (1.490, 1.597 and 1.612 Å) bond lengths. For dimethyl boranophosphate, one potassium ion was found near one of the oxygen atoms at a distance of 2.66 Å. Based on a comparison of the bond lengths of dimethyl boranophosphate salt with BPi, we assume that the BPi bears two H atoms, which were not found in the crystallographic data.

The shortest P—O bond (1.524 Å) indicates a partial double-bond character, and is in accordance with values found in the structures of phosphate diesters (1.47-1.51 Å) and monoesters (1.49-1.53 Å). This P—O bond is significantly longer than the bond observed in phosphate triesters (1.38-1.44 Å) (Corbridge, 1974).

2(viii) Infra-red (IR) Spectroscopy of 2a and 2b.

Figure 4A:
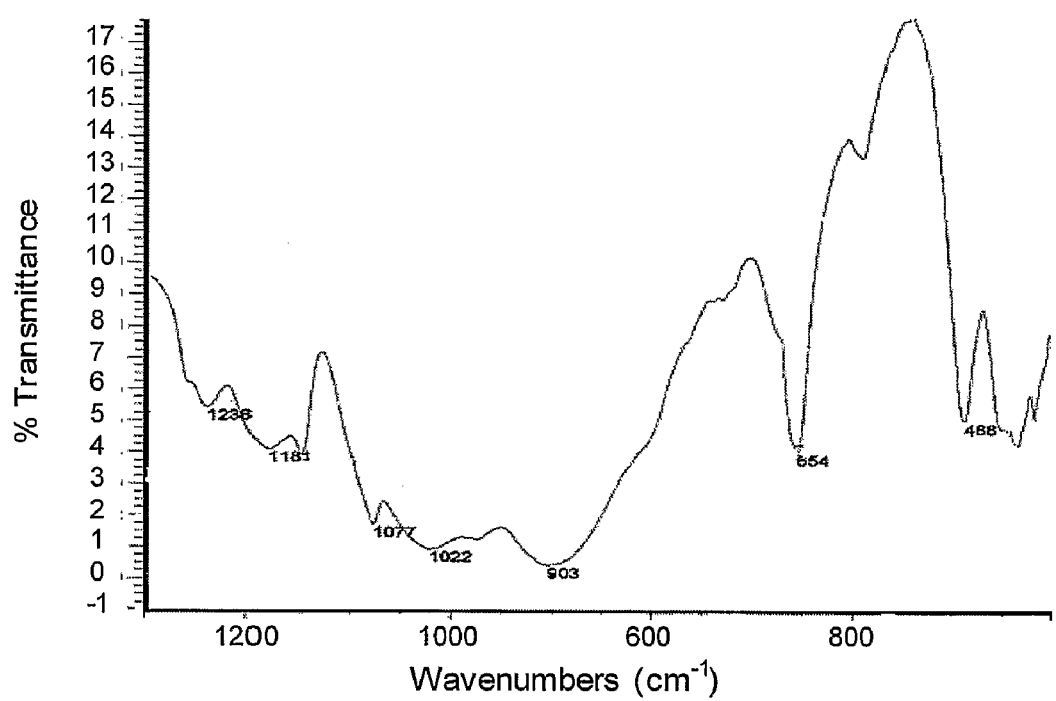
FIGS. 4A-4B depict the IR spectra of: (4A) BPi 2a (KBr pellet; 1300-400 cm$^{-1}$), and (4B) BPi 2c (germanium cell; 1300-1100 cm$^{-1}$; cutoff: 680 cm-1): curve A—methanolic solution, curve B—aqueous solution, curve C—neat sample.

The IR spectra of 2a or 2b in KBr pellet indicated characteristic bands for P—B and B—H in addition to bands associated with P—OH and P=O (FIG. 4A). Specifically, three absorptions at 2350, 2381, 2407 cm$^{-1}$ (s) (not shown) correspond to B—H stretches, and the absorption at 654 cm$^{-1}$ (m) is the P—B stretch (Corbridge, 1995). We also based our IR assignment on quantum mechanical calculations as follows. The boranophosphate anion was optimized using the B3LYP functional in conjunction with the 6–31+6(d) basis-set. Frequency calculation was performed to obtain the IR spectrum and the harmonic vibrational frequencies were scaled by a factor of 0.9614. The calculations employed the Gaussian 98 program (Frisch et al., Gaussian 98 (Revision A.7), Gaussian, Inc.,Pittsburgh, Pa., 1998). Typical absorptions were observed for P—OH and P=O stretches, 900-1080 cm$^{-1}$, and at 1140-1250 cm$^{-1}$, respectively.

Figure 4B:
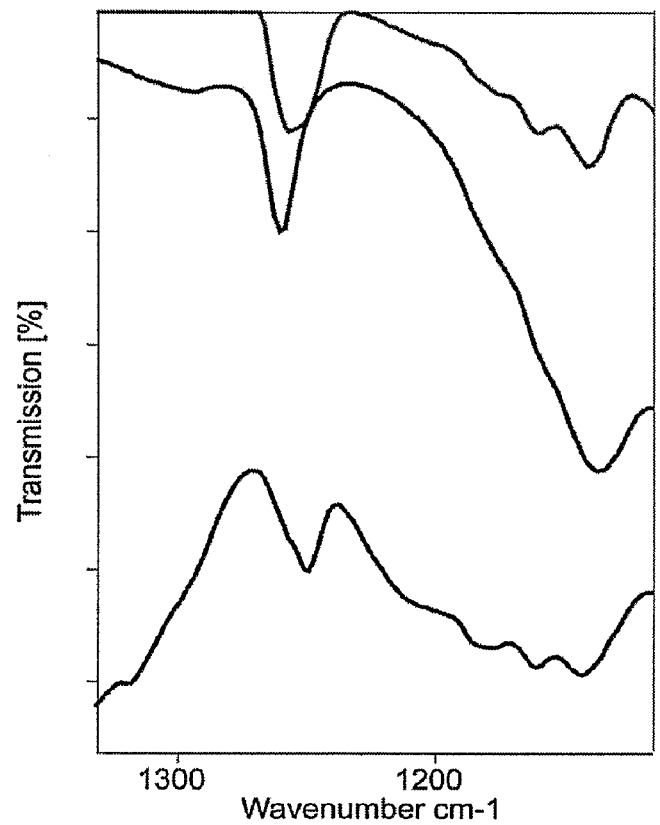

For an evaluation of the effects of the solvents on H-bonds between BPi ions, IR spectra of BPi, 2a, in aqueous and methanolic solutions (see below "H-bonding of Bpi") were measured in a germanium cell and compared to the corresponding spectrum of a neat sample of Bpi (FIG. 4B). Comparison of those spectra indicated only minor differences. For instance, a shift of about 10 cm$^{-1}$ to lower frequencies was observed for the P=O stretch of BPi, either in the neat sample or in MeOH, relative to BPi in aqueous solution. This shift is probably due to H-bonding based clustering in the neat sample and MeOH. The typical fine-structure for the P=O stretch in a neat sample of BPi, in the range of 1144-1178 cm$^{31}$ $^{1}$, which is possibly also due to H-bonded clusters, is lost in water. The corresponding spectrum in MeOH appears as an average of the neat sample and aqueous solution spectra, probably indicating the presence of both BPi clusters and solvent H-bonded species.

Example 3

Chemical Properties of Compounds 2a, 2b and 2c

3(i) Acid-base Properties.

The acid-base character of BPi was studied by $^{31}$P NMR—monitored pH-titration, as described in Experimental, (v). The chemical shift of compound 2a was plotted against pH (FIG. 5A). For the pH range of 4.8-13.2, two inflection points were observed. The second derivatives of the fitted function provided two pK$_a$ values: 7.12 (FIG. 5B) and 12.54, with R$^2$ values of 0.999 and 0.997, respectively. These values are similar to the corresponding values of the second and third protonation equilibria of phosphoric acid (7.21 and 12.67), and are higher than those for phosphorus acid (H-phosphonate; 1.8 and 6.2).

3(ii) Stability of BPi.

BPi is stable in neutral and basic solutions. For instance, after 48 h at room temperature at pH 13.7, no degradation of BPi was observed by $^{31}$P NMR spectroscopy. BPi is also relatively stable in acidic solution at pH>2. At pH 2, BPi slowly degrades slowly to phosphorus acid at a rate of 7×10$^{-7}$ sec$^{-1}$, R$^2$=1.00 (t$_{1/2}$ =275 h), as monitored by $^{31}$P NMR spectroscopy.

Under highly acidic conditions (pH<2), the evolution of H$_2$ is clearly observed, the P—B bond is cleaved, and boric acid is formed together with phosphorus acid (Scheme 3) (Li et al., 1996). Phosphorus acid was observed in the $^{31}$P NMR spectroscopy as a doublet at δ=3.5 ppm (J=633 Hz). The borane reacts with water to liberate hydrogen gas and boric acid.

The stability of inorganic boranophosphate, resulting from neutral hydrolysis of thymidine 5'-boranomonophosphate at 50° C., has been reported earlier (Li et al., 1996).

3(iii) H-bonding of BPi.

Solutions of 2b or 2c in organic solvents (DMF, CH$_3$CN, CHCl$_3$ and even MeOH) show unexpected $^{31}$P NMR spectra. Product 2b in MeOH apparently consists of three different but pattern-related signals. The signals with chemical shifts of δ=80.0 (A), 86.2 (B) and 90.8 (C) ppm, each had an identical BPi-typical pattern (FIG. 6).

Several minutes after the dissolution of 2b in MeOH, signals A, B, and C are observed in the $^{31}$P NMR spectrum, with A and B as the major peaks (C constitutes ca. 5% of the mixture). The composition of the initial mixture is time-dependent due to interconversion of the species. When monitoring this process with 0.14 M 2b in CD$_3$OD (ε=33) for 160 h at room temperature, we noted the conversion of A and B to C, with a final C:B ratio of 4.4:1 (A disappeared completely). The $^1$H-coupled $^{31}$P NMR spectrum indicated H-splitt quadruplet signals for B and C, namely, no D-H exchange occurred.

Figure 6:
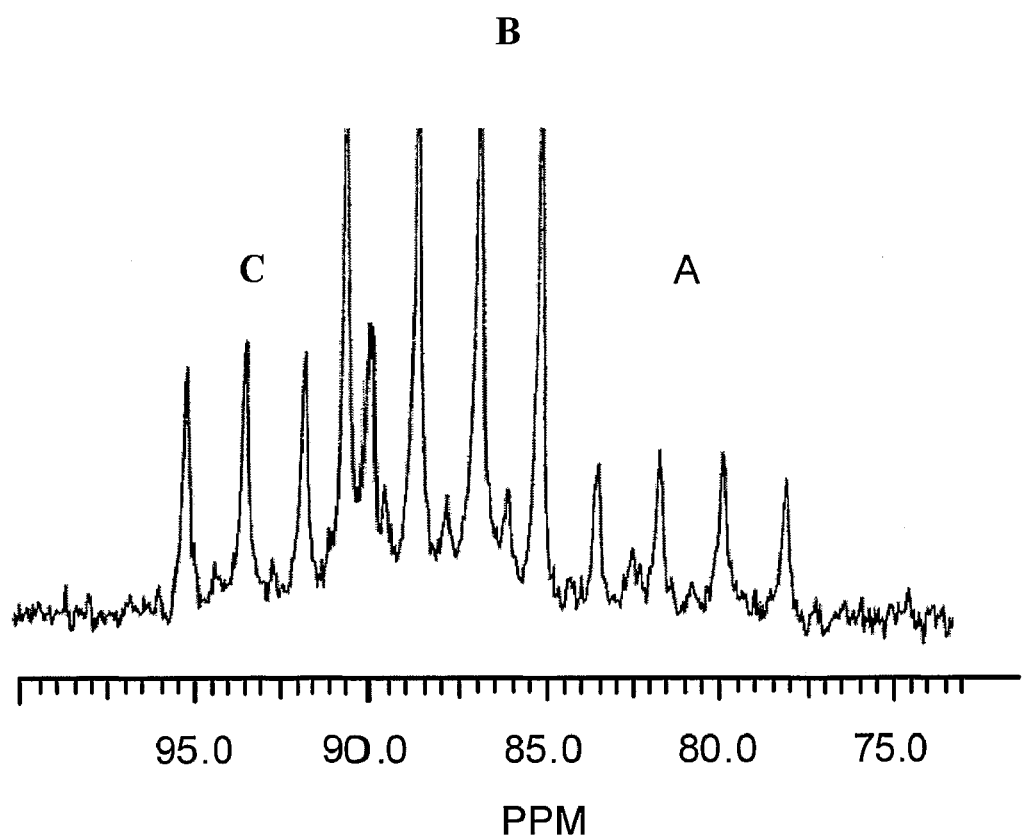
FIG. 6 shows the $^{31}P$ NMR spectrum of BPi 2b in methanolic solution.

A spectrum similar to the one shown in FIG. 6, and time-dependent interconversion of the species, was observed for 2b in DMF, CH$_3$CN, and CHCl$_3$.

The possibility that the additional BPi-like species are the corresponding mono- or di-methyl esters, due to a reaction of 2b with MeOH, was ruled out because their $^{13}$C and $^1$H NMR spectra in CDCl$_3$ were devoid of a methyl ester signal.

The three signals seen in $^{31}$P NMR spectrum of 2c in organic solvents converged into one, probably A (δ=79.8 ppm), after solvent evaporation and dissolution in D$_2$O. Therefore, the possibility that signals B and C are due to boranophosphate anhydrides, resulting from 2c in the NMR sample is unlikely.

To assess the possibility of observing different H-bond-clustered species on the NMR timescale, we measured the $^{31}$P NMR spectrum of the parent phosphate bis(tributylammonium) salt in benzene, where clustering is known to occur (Peppard et al., 1958; Peppard et al., 1957). Indeed, three signals were clearly observed at δ=3.63, 3.23, and 2.93 ppm, demonstrating that different H-bonded phosphate clusters can be detected by $^{31}$P NMR spectroscopy. These three phosphate signals, seen in benzene, converged into one in acetonitrile and MeOH, indicating the collapse of the Pi clusters in polar/protic solvents.

Figure 5:
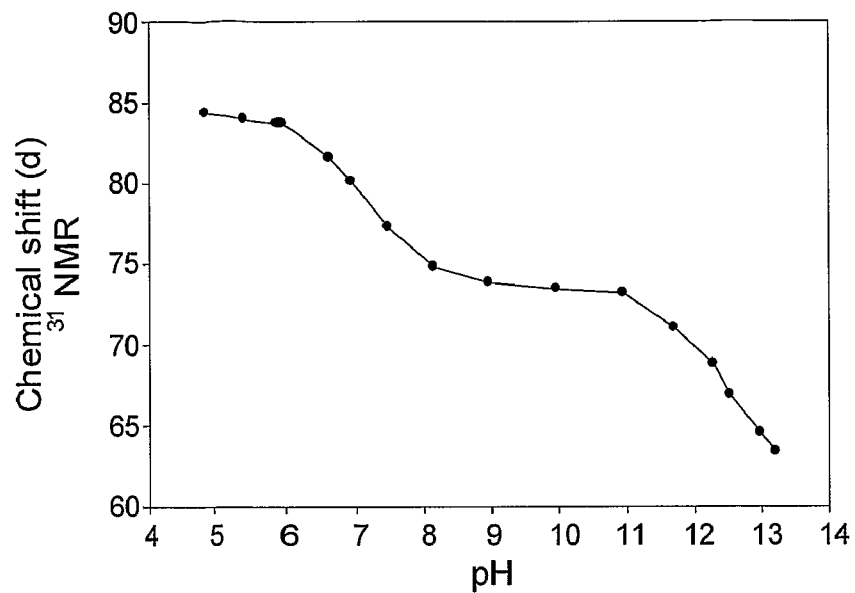
FIG. 5 shows determination of pKa values of BPi; plot of BPi's $^{31}P$ NMR chemical shift in $H_2O$ as a function of the pH; two inflection points are observed in the pH range of 4.87-13.20.

Based on our observations of the pH-dependent chemical shift of BPi (FIG. 2), and on the determination of BPi's acidity constants (FIG. 5), we propose the following assignment of signals A, B and C. Signal A corresponds to the monomeric BPi, whose chemical shift at δ=80 ppm indicates that half the BPi monomer population bears two protons, and the other half bears one proton (FIG. 5). Signal B, at δ=86 ppm, corresponds to a BPi moiety that has one BPi H-bonded neighbor. Namely, signal B could result both from BPi dimers and higher clusters (Scheme 4). In these cases, each BPi is associated with an additional proton (Bu$_3$NH$^+$ ions neutralize the negative charges). Therefore, the chemical shift of the BPi dimer shifts downfield (δ=86 ppm, as at pH 4.7). As indicated by signal C, BPi also forms clusters, corresponding to a BPi moiety that has two H-bonded BPi neighbors (Scheme 4). A BPi moiety in the middle of a cluster is associated with three protons, resulting in an additional downfield shift to δ=91 ppm, corresponding to that of BPi at pH=2.

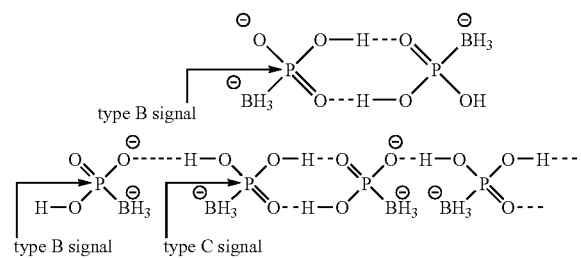

Scheme 4

Small H-bonded clusters (i.e. dimers and trimers) are formed almost instantaneously. This is probably the stage of nucleation. Once a critical nucleus is formed, a slow process of high-order clustering occurs. At this stage the concentration of A in solution is drastically reduced. This H-bonding based clustering mechanism is also supported by the observation that, upon evaporation of the organic solvent from the species mixture and dissolution in water, only A is detected.

The fact that BPi forms clusters even in MeOH, whereas Pi forms clusters only in benzene, implies that $BH_3$ may play a role in the pre-organization of the BPi clusters. The lipophilic $BH_3$ moieties possibly form the core of the cluster due to hydrophobic interactions (in MeOH). This core is then further stabilized by P—O$^-$ . . . HO—P H-bonds.

3(iv) Reactions of BPi with Selected Reagents.

The reactivity of BPi towards various organic and inorganic reagents was explored as part of the characterization of BPi's chemical nature. These reagents include: aqueous acid solution, nitrile, amide, carbodiimide, pyridine and imidazole, tosyl chloride, phosphorous oxychloride, $H_2$, and $Zn^{2+}$ and $Mg^{2+}$ ions.

Although $BH_3$, in complexes with a variety of sulfur/amine/oxygen compounds, is an efficient reducing agent, its reducing nature is drastically altered in Bpi. For instance, while hydrid transfer from "$BH_3$" to water occurs readily, the $BH_3$ moiety in BPi transfers hydride only in a highly acidic solution (pH<2). Likewise, while $BH_3$. THF complex readily reduces nitriles and amides to the corresponding amines (Brown, 1972), the borane moiety in BPi does not reduce acetonitrile and dimethyl formamide, as evidenced by the complete stability of BPi in these solutions.

A carbodiimide reagent is used for the condensations of phosphate to provide the corresponding phosphoric anhydride. The reaction of 2a with an excess of 1-(3-dimethylaminopropyl)-3-ethylcarbodiimide (EDC) was explored in water (pH 6.5), at 37° C. for 4 h. The addition of EDC to BPi resulted in excessive loss of this compound, due to complete P—B bond cleavage of 2a, to yield phosphorus acid (72% of 2a was degraded after 4 h, based on the $^{31}$P NMR spectrum). This finding is in contrast to diethylphosphite (cyano- or methoxycarbonyl)borane analogues, which are stable to dicyclohexylecarbodiimide (DCC) (Vyakaranam et al., 2002).

The P—B bond was also found to be sensitive to catalytic hydrogenation. Thus, when compound 9 was subjected to hydrogenation (over Pd/C), the P—B bond was also reduced, yielding phosphorus acid.

The reactivity of BPi with imidazole and pyridine was studied. Specifically, a solution of BPi with 2 or 10 equiv. of imidazole in $CD_3OD$ remained unchanged for 96 h, based on the $^{31}$P NMR spectra. Likewise, only a negligible cleavage of the P—B bond was observed after 113 h for a solution of BPi in pyridine. BPi is apparently more stable to imidazole and pyridine than the related analogue, tetramethyl boranopyrophosphate. The reaction of 5'-DMT-2'-deoxy-thymidine with tetramethyl boranopyrophosphate in the presence of N-methylimidazole was reported to proceed with the partial removal of the borane group. Likewise, when pyridine was used as a solvent, partial removal of the borane group was observed (Wada et al., 2002).

The presence of divalent metal ions such as $Zn^{2+}$ and $Mg^{2+}$ in DMF and water for 48 h and 4 h, respectively, left BPi unchanged.

Whereas dimethyl boranophosphate monopotassium salt, 3, plays the role of an efficient nucleophile (Imamoto et al., 1997), the related BPi is a poor nucleophile. Thus, when BPi was treated with tosyl chloride or mesyl chloride (with or without amine) in acetonitrile for 24 h, even at 60° C., no reaction occurred. Likewise, the reaction of BPi with phosphorus oxychloride and its derivatives (P(O)Cl$_2$R) yielded no product.

REFERENCES

Agrawal, S. *Biochim. Biophys. Acta* 1999, 1489, 53-67.
Blackburn, G. M. *Chem. Ind.* 1981, 134.
Blackburn, G. M.; England, D. A. Kolkman, F. *Chem. Commun.* 1981, 930-932.
Blackburn, G. M. Brown, D.; Martin, S. J.; Parratt, M. J. *J Chem. Soc. Perkin Trans.* 1 1987, 181-186.
Brown, H. C. *Borane in Organic Chemistry.* Cornell University Press: Ithaca, 1972, pp 230-5.
Bundgaard, H.; Hansen, *J. Int. J. Pharm.* 1981, 9, 273-283.
Conolly, B. A.; Eckstein, F. *Biochemistry,* 1982, 21, 6158-6167.
Corbridge D. E. C. *The Structural Chemistry of Phosphorous*; Elsevier: Amsterdam, 1974.
Corbridge D. E. C. *Phosphorous: An Outline of its Chemistry, Biochemistry and Technology*; Studies in Inorganic Chemistry, Vol 20, Elsevier: Amsterdam, 1995; pp 1141-2.
Cullis, P. M.; Fawcett, G. A.; Harger, M. J.; Lee, M. *J Am. Chem. Soc.* 2001, 123, 4147-54.
Eckstein, F. *Ann. Rev. Biochem.* 1985, 54, 367-402.
Eckstein, F. *Angew Chem. Int. Ed. Engl.* 1983, 22, 423-439.
Eckstein, F. *Antise. Nucl. Acid Drug Dev.* 2000, 10, 117-121.
El Seoud, O. A.; Ruasse, M.-F.; Rodrigues, W. A. *Perkin Trans.* 2, 2002, 1053-1058.
Engel, R. *Chem. Rev.* 1977, 77, 349-367.
Gerlt, J. A.; Reynolds, M. A.; Demou, P. C.; Kenyon, G. L. *J Am. Chem. Soc.* 1983, 105, 6469-6474.
Harris, R. K. *Nuclear Magnetic Resonace Spectroscopy: A Physicochemical View*. Longman Scientific and Technical, Somerset: N.J., 1986.
He, K.; Porter, K. W.; Hasan, A.; Briley, J. D.; Shaw, B. R. *Nucleic Acids Res.* 1999, 27, 1788-1794
Imamoto, T.; Nagato, E.; Wada, Y.; Masuda, H.; Yamaguchi, A.; Uchimaru, T. *J Am. Chem. Soc.* 1997, 119, 9925-9926.
Jaffe, E. K.; Cohn, M. *Biochemistry,* 1978, 17, 652-657.
Li, H.; Hardin, C.; Ramsay Shaw, B. *J Am. Chem. Soc.* 1996, 118, 6606-6614.
Longeau, A.; Knochel, P. *Tetrahedron Lett.* 1996, 37, 6099-6102.
Nahorski, S. R.; Potter, V. B. L. *Trends Pharmacol. Sci.* 1989, 10, 139-144.
Nahum, V.; Ubl, J.; Reiser, G.; Levesque S.; Beaudoin, A. R.; Fischer B. *J Med. Chem.* 2002, 45, 5384-5396.
Peppard, D. F.; Ferraro, J. R.; Mason, G. W.; J. *Inorg. Nuclear Chem.* 1958, 7, 231-244.
Peppard, D. F.; Ferraro, J. R.; Mason, G. W.; J. *Inorg Nuclear Chem.* 1957, 4, 371-372.
Porter, K. W.; Briley, D. J.; Shaw, B. R. *Nucleic Acids Res.* 1997, 25, 1611-1617.
Rait, V.; Sergueev, D. S.; Summers, J. S.; He, K.; Huang, F.; Krzyzanowska, B.; Shaw, B. R. *Nucleosides Nucleotides* 1999, 18, 1379-1380.
Roumaniuk, P. J.; Eckstein, F. *J Biol. Chem.* 1981, 256, 7322-7328.
Saxena, S. Ind. *J. Chem. Section A: Inorg. Bioinorg Phys. Theor. Anal. Chem.* 2002, 41A, 718-722.
Sergueeva, Z. A.; Sergueev, D. S.; Ribeiro, A. A.; Summers, J. S.; Shaw, B. R. *Helv. Chim. Acta* 2000, 83, 1377-1391, and references therein.
Shaw, B. R.; Sergueev, D.; He, K.; Porter, K.; Summers, J. S.; Sergueeva, Z.; Rait, V. *Methods in Enzymol.* 2000, 313, 226-257.

Shaw, B. R.; Madison, J.; Sood, A.; Spielvogel, B. F. *Methods in Molecular Biology;* 1993; Vol. 20, Chapter 11, 225-243.

Sood, A.; Sood, C. K.; Hall, I. H.; Spielvogel, B. F. *Tetrahedron,* 1991, 47, 6915-6930.

Sood, A.; Ramsay Shaw, B.; Spielvogel, B. F. *J Am. Chem. Soc.* 1990, 112, 9000-9001.

Spielvogel, B. F.; Sood, A.; Shaw, B. R.; Hall, I. H.; Fairchild, R. G.; Laster, B. H.; Gordon, C. *Prog. Neutron Capture Therap. Cancer,* 1992, 211-213

Stein, C. A. *Chem. Biol.* 1996, 3, 319-323.

Summers, J. S.; Roe, D.; Boyle, P. D.; Colvin, M.; Shaw, B. R. *Inorg. Chem.* 1998, 37, 4158-4159.

Summers, J. S.; Shaw, B. R. *Curr. Med. Chem.* 2001, 8, 1147-1155.

Vyakaranam, K.; Rana, G.; Spielvogel, B. F.; Maguire, J. A.; Hosmane, N. S. *Nucleosides, Nucleotides and Nucleic Acids,* 2002, 21, 581-598.

Wada, T.; Shimizu, M.; Oka, N.; Saigo, K. *Tet. Lett.* 2002, 43, 4137-4140

Westheimer, F. H. *Science* 1987, 1173-1178.

Westheimer, F. H. *Phosphorus Chemistry—Developments in American Science.* Walsh, E. N.; Griffith, E. J.; Parry, R. W.; Quin, L. D. Eds. ACS Symposium Series 486ACS, Washington D.C., 1992.

Zhang, J.; Terhorst, T.; Matteucci, M. D. *Tet. Lett.* 1997, 38, 4957-4960.

What is claimed is:

1. A method for the preparation of an inorganic boranophosphate salt of the general formula 2:

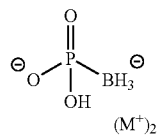

wherein M is a counterion, comprising reacting tris(trimethylsilyl)-phosphite with borane-dimethylsulfide complex of the formula $BH_3 \cdot SMe_2$, in dry acetonitrile under inert gas, and treating the formed intermediate with the suitable base MOH in water or methanol, thus obtaining the desired salt.

2. The method according to claim 1, wherein said base is methanolic ammonia or an aqueous $NH_4OH$ solution, thus resulting in the ammonium salt, wherein M is $NH_4^+$.

3. The method according to claim 1, wherein said base is tributylamine, $Bu_3N$, in methanol, thus resulting in the tributylammonium salt, wherein M is $Bu_3NH^+$.

4. The method according to claim 1, comprising treating the intermediate with triethylammonium bicarbonate buffer, thus resulting in the $Et_3NH^+$ salt.

5. The method according to claim 1, wherein the counterion M is ammonium ($NH4^+$) or an inorganic cation derived from an alkali, alkaline earth or transition metal.

6. The method according to claim 5, wherein the counterion M is $Na^+$, $K^+$, $Li^+$, $Ca^{++}$, $Mg^{++}$, $Cu^{++}$, $Fe^{++}$, $Fe^{+++}$, $Co^{++}$, $Zn^{++}$, $Pd^{++}$, or $Ag^+$.

7. The method according to claim 1, wherein the counterion M is an organic cation derived from an amine of the formula $R_3NH^+$, wherein R is $C_1$-$C_{18}$, alkyl, phenyl, heteroaryl or two of the Rs together with the nitrogen atom to which they are attached form a 3-7 membered ring optionally containing a further heteroatom selected from the group consisting of N, S and O.

8. The method according to claim 7, wherein each R is $C_1$-$C_6$ alkyl, optionally ethyl, propyl or butyl.

* * * * *